(12) United States Patent
Jolly et al.

(10) Patent No.: US 9,480,838 B2
(45) Date of Patent: Nov. 1, 2016

(54) COCHLEAR ELECTRODE WITH APICAL LATERAL WALL SECTION AND BASAL MODIOLAR HUGGING SECTION

(71) Applicant: MED-EL Elektromedizinische Geraete GmbH, Innsbruck (AT)

(72) Inventors: Claude Jolly, Innsbruck (AT); Anandhan Dhanasingh, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/609,590

(22) Filed: Jan. 30, 2015

(65) Prior Publication Data

US 2015/0148736 A1    May 28, 2015

Related U.S. Application Data

(63) Continuation-in-part of application No. 14/514,963, filed on Oct. 15, 2014.

(60) Provisional application No. 61/890,923, filed on Oct. 15, 2013.

(51) Int. Cl.
*A61N 1/05* (2006.01)
*A61N 1/36* (2006.01)
*A61M 31/00* (2006.01)

(52) U.S. Cl.
CPC .......... *A61N 1/0541* (2013.01); *A61M 31/002* (2013.01)

(58) Field of Classification Search
CPC ................ A61N 1/0541; A61N 1/36032
See application file for complete search history.

(56) References Cited

U.S. PATENT DOCUMENTS

| | | | | |
|---|---|---|---|---|
| 5,769,881 A | * | 6/1998 | Schroeppel | A61N 1/056 600/375 |
| 2003/0097121 A1 | * | 5/2003 | Jolly | A61M 5/14276 604/891.1 |
| 2010/0069999 A1 | * | 3/2010 | Jolly | A61N 1/0541 607/57 |
| 2010/0179626 A1 | * | 7/2010 | Pilarski | A61B 17/3468 607/116 |

* cited by examiner

*Primary Examiner* — Edward Moran
*Assistant Examiner* — Natasha Patel
(74) *Attorney, Agent, or Firm* — Sunstein Kann Murphy & Timbers LLP

(57) ABSTRACT

An implantable electrode array for a cochlear implant has an array trunk that extends along a center axis from an insertion opening in an outer surface of a patient cochlea into the scala tympani. An apical section extends along the center axis from a distal end of the array trunk and a basal branch is separate from the array trunk and extends back from the distal end of the array trunk towards the insertion opening. The apical section follows along an outer lateral wall of the scala tympani during surgical insertion to attain a final insertion position towards the outer lateral wall in an apical portion of the scala tympani beyond a first basal turn of the cochlea. The basal branch attains a final insertion position towards an inner modiolar wall by the first basal turn of the cochlea with the basal branch stimulation contacts facing the inner modiolar wall.

11 Claims, 6 Drawing Sheets

COCHLEAR ELECTRODE WITH APICAL LATERAL WALL SECTION AND BASAL MODIOLAR HUGGING SECTION

This application is a continuation in part of U.S. patent application Ser. No. 14/514,963, filed Oct. 15, 2014, which claims priority from U.S. Provisional Patent Application 61/890,923, filed Oct. 15, 2013, both of which are incorporated herein by reference in their entireties.

FIELD OF THE INVENTION

The present invention relates to medical implants, and more specifically to an implantable electrode for use in cochlear implant systems in patients having a malformed cochlea.

BACKGROUND ART

A normal ear transmits sounds as shown in FIG. 1 through the outer ear 101 to the tympanic membrane (eardrum) 102, which moves the bones of the middle ear 103 (malleus, incus, and stapes), which in turn vibrate the oval window and round window openings of the cochlea 104.

The cochlea 104 is a long narrow duct wound spirally about its axis for approximately two and a half turns. FIG. 2 shows a cross-sectional view of the cochlea 104 in which the spiral shape is evident. The first full turn of the cochlea 104 is referred to as the basal turn, with the turns beyond that referred to as the apical turns. At each turn, the cochlea 104 has an upper duct, the scala vestibuli 201, and a lower duct, the scala tympani 202, which are separated by a middle duct, the scala media 203 that contains the sound sensing neural ends of the auditory nerve that lies along the center axis of the cochlea, referred to as the modiolar 204. The scala tympani 202 has an inner modiolar wall 205 and an outer lateral wall 206. In response to received sounds transmitted by the middle ear 103, the fluid-filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea. In such cases a cochlear implant is an auditory prosthesis which uses an implanted stimulation electrode to bypass the acoustic transducing mechanism of the ear and instead stimulate auditory nerve tissue directly with small currents delivered by multiple electrode contacts distributed along the electrode.

FIG. 1 also shows some components of a typical cochlear implant system which includes an external microphone that provides an audio signal input to an external signal processing stage 111 where various signal processing schemes can be implemented. The processed signal is then converted into a digital data format, such as a sequence of data frames, for transmission into the implant stimulator 108. Besides extracting the audio information, the implant stimulator 108 also performs additional signal processing such as error correction, pulse formation, etc., and produces a stimulation pattern (based on the extracted audio information) that is sent through connected wires 109 to an implanted electrode array 110. Typically, this electrode array 110 includes multiple electrodes on its surface that provide selective stimulation of the cochlea 104. For a variety of reasons, the electrode array 110 is usually implanted into the scala tympani 202.

The electrode array 110 contains multiple electrode wires embedded in a soft silicone body referred to as the electrode carrier. The electrode array 110 needs to be mechanically robust, and yet flexible and of small size to be inserted into the cochlea 104. The material of the electrode array 110 also needs to be soft in order to minimize trauma to neural structures of the cochlea 104. But an electrode array 110 that is too floppy tends to buckle too easily so that the electrode array 110 cannot be inserted into the cochlea 104 up to the desired insertion depth. A trade-off needs to be made between a certain stiffness of the electrode array 110 which allows insertion into the cochlea 104 up to the desired insertion depth without the array buckling, and certain flexibility of the electrode array 110 which keeps mechanical forces on the internal structures of the cochlea 104 low enough.

Recent developments in electrode array designs and surgical techniques are directed towards minimizing the trauma of the surgical implantation of the array. For preservation of residual hearing it is of particular importance to preserve the natural intra-cochlear structures. Therefore, the size and mechanical characteristics of the electrode array are critical parameters for the best patient benefit. Some electrode array designs are pre-curved, though a drawback of that approach is that a special electrode insertion tool is needed which keeps the electrode array straight until the point of insertion.

As documented by Erixon et al., *Variational Anatomy of the Human Cochlea: Implications for Cochlear Implantation*, Otology & Neurotology, 2008 (incorporated herein by reference), the size, shape, and curvature of the cochlea varies greatly between individuals, meaning that an electrode array must match a wide range of scala tympani geometries. Furthermore, recently published research by Verbist et al., *Anatomic Considerations of Cochlear Morphology and Its Implications for Insertion Trauma in Cochlear Implant Surgery*, Otology & Neurotology, 2009 (incorporated herein by reference) has shown that the human scala tympani does not incline towards the helicotrema at a constant rate, but rather there are several sections along the scala tympani where the slope changes, sometimes even becoming negative (i.e. downwards). The location and grade of these changes in inclination were also found to be different from individual to individual. Consequently, electrode arrays should be highly flexible in all directions in order to adapt to individual variations in curvature and changes in inclination of the scala tympani for minimal trauma implantation.

FIGS. 3A-3B are x-ray photographs depicting the relationship between an implanted electrode array 301 and the side walls of the scala tympani. The electrode array 301 typically gets pushed outward during implantation to lie against the outer lateral wall 302 of the scala tympani. As can be seen in FIG. 3A, the cross-sectional size of the scala tympani is great enough compared to the size of the electrode array 301 so that the outer lateral wall location of the array is relatively far from the inner modiolar wall 303 (especially within the first basal turn). In some cases, as shown in FIG. 3B, the angle of the array entry into the cochlea brings the electrode array 301 closer to the modiolar wall 303 near the entry point, but that only lasts for a very short section before the distance again increases.

Electrode arrays that lie close to the inner modiolar wall of the cochlear scala tympani are advantageous over the more typical free-fitting electrode arrays that lie against the outer lateral wall in-terms of power consumption and effectiveness in stimulating the spiral ganglion cells of the modiolus. On the other hand, modiolar hugging electrode arrays create greater trauma during insertion (especially via a cochleostomy opening) and also during explantation.

Modiolar hugging electrode arrays known in the prior art are often pre-curved and required a positioning stylet for safe introduce it into the cochlea (e.g., U.S. Pat. No. 5,545, 219, U.S. Pat. No. 6,125,302, and U.S. Pat. No. 6,374,143). Other existing perimodiolar hugging electrode arrays require some additional structural elements to ensure placement of the electrode array close to the inner modiolar wall after insertion. However, after insertion there is no opportunity for the surgeon to correct and optimize the position of the electrode array.

U.S. Pat. No. 6,498,954 describes a cochlear implant electrode array with a leading section that is attached to the distal end of the electrode array. Two separate cochleostomies are drilled, one at the base and another separate one at the apex of the cochlea. The electrode leading section then is inserted through the basal cochleostomy and advanced towards the apical cochleostomy. A forward end of the leading section is then pulled through the apical cochleostomy which causes the electrode array to be pulled into the cochlea. The leading section must be the leading section must relatively stiff in order to properly move the leading section through the interior of the cochlea from base to apex.

SUMMARY OF THE INVENTION

Embodiments of the present invention are directed to an implantable electrode array for a cochlear implant. An array trunk that extends along a center axis from an insertion opening in an outer surface of a patient cochlea into the scala tympani. An apical section extends along the center axis from a distal end of the array trunk and a basal branch is separate from the array trunk and extends back from the distal end of the array trunk towards the insertion opening. The apical section and the basal branch both have stimulation contacts for delivering electrical stimulation signals to adjacent neural tissue. The stiffness and geometry of the apical section are configured so that the apical section follows along an outer lateral wall of the scala tympani during surgical insertion to attain a final insertion position towards the outer lateral wall in an apical portion of the scala tympani beyond a first basal turn of the cochlea. The stiffness and geometry of the basal branch are configured so that the basal branch attains a final insertion position towards an inner modiolar wall by the first basal turn of the cochlea with the basal branch stimulation contacts facing the inner modiolar wall.

The outer surface of the apical section and the outer surface of the basal branch may meet in a smooth continuous transition zone. The array trunk and the basal branch may each have semi-circular cross-sections with adjacent flat surfaces. The array trunk may have an outer surface configured to post-surgically release a therapeutic substance to inhibit tissue ingrowth between the array trunk and the basal branch.

In some embodiments there may be a retraction feature fitting between the array trunk and the basal branch configured to facilitate extraction of the electrode array from the scala tympani. And there may be an outer insertion tube configured to fit over the basal branch and the array trunk for insertion into the cochlea, and retractable back through the insertion opening after insertion of the electrode array into the cochlea to allow the basal branch to open away from the array trunk toward the inner modiolar wall. In such arrangements, the insertion tube may contain a longitudinal slit along its outer surface for removal of the insertion tube from the electrode lead after retraction and/or include one or depth indicator marks along its outer surface. And there may be an internal support wire within the basal branch that biases the basal array branch away from the array trunk toward the inner modiolar wall.

Embodiments may also have an arrangement of magnetic elements including an array trunk magnetic element located on the outer surface of the array trunk facing the basal branch, and a basal branch magnetic element located on the outer surface of the basal branch opposite and facing the array trunk magnetic element. In such an embodiment, the magnetic elements are arranged with like magnetic polarities facing each other so as to promote placement of the basal branch towards the modiolar wall Embodiments also include a complete cochlear implant system having an implantable electrode array according to any of the above.

DETAILED DESCRIPTION OF SPECIFIC EMBODIMENTS

Embodiments of the present invention are directed to implantable electrode arrays for cochlear implants that is very atraumatic, but also very effective in terms of focused stimulation. This is achieved with an electrode array that has two different sections. An apical section of the electrode array remains straight to be atraumatic and protect the delicate anatomical structures. A basal branch of the electrode array is designed to be positioned close to the modiolar window.

Figure 1:
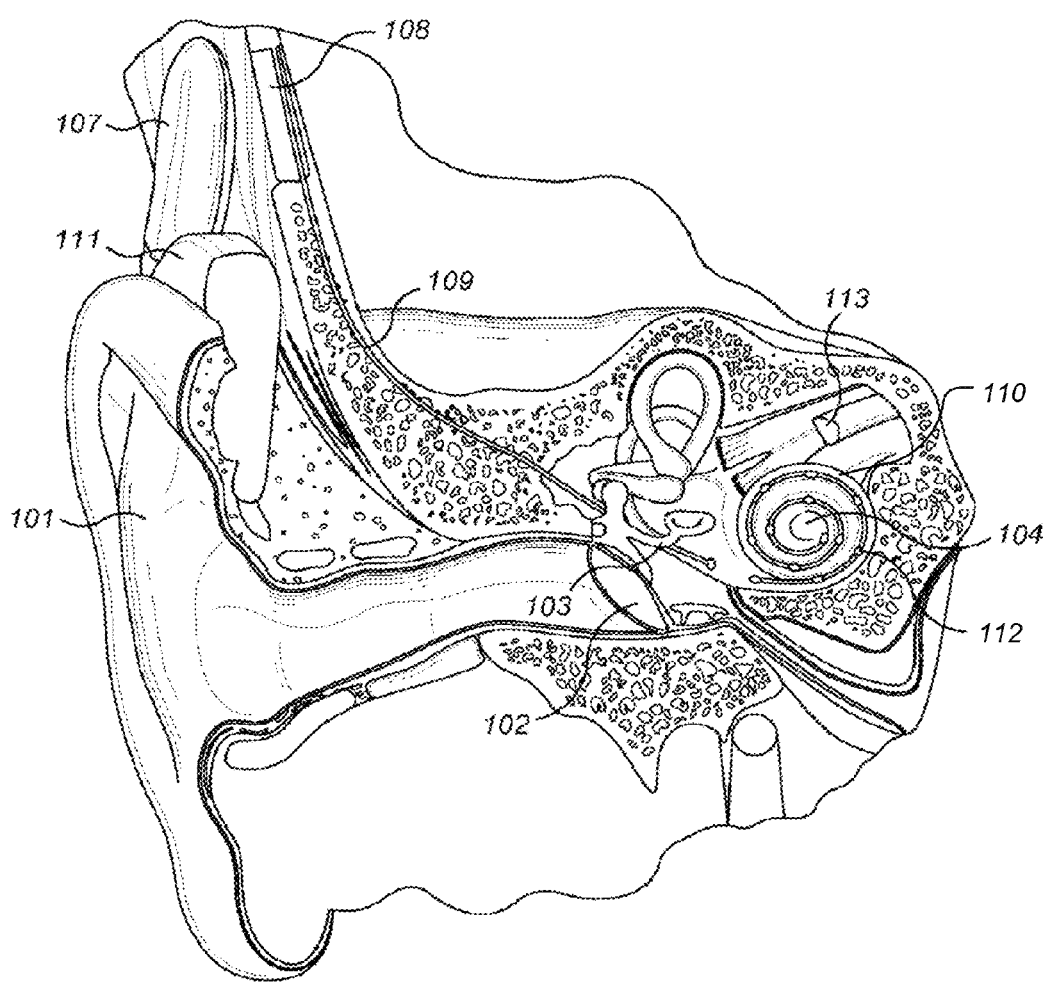
FIG. 1 shows elements of a human ear having a typical cochlear implant system.
Figure 2:
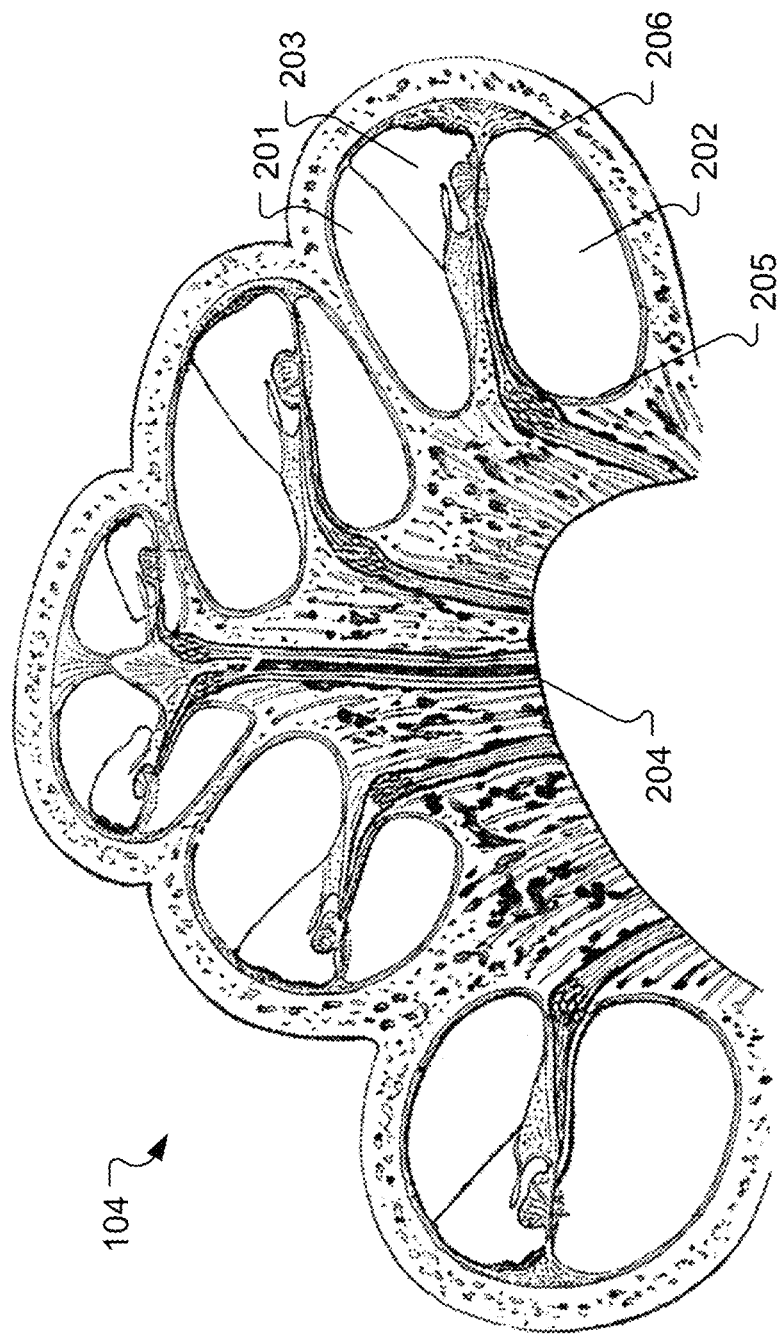
FIG. 2 shows a cross-sectional view of a typical human cochlear with details of various anatomical structures.
Figure 3A:
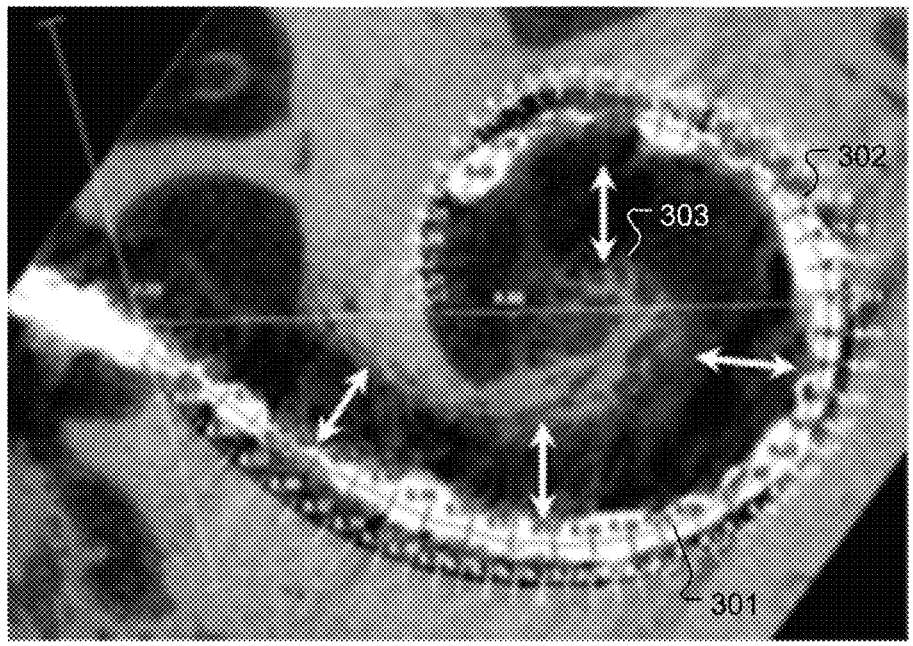
FIGS. 3A-3B are x-ray photographs depicting the relationship between an implanted electrode array and the side walls of the scala tympani.
Figure 3B:
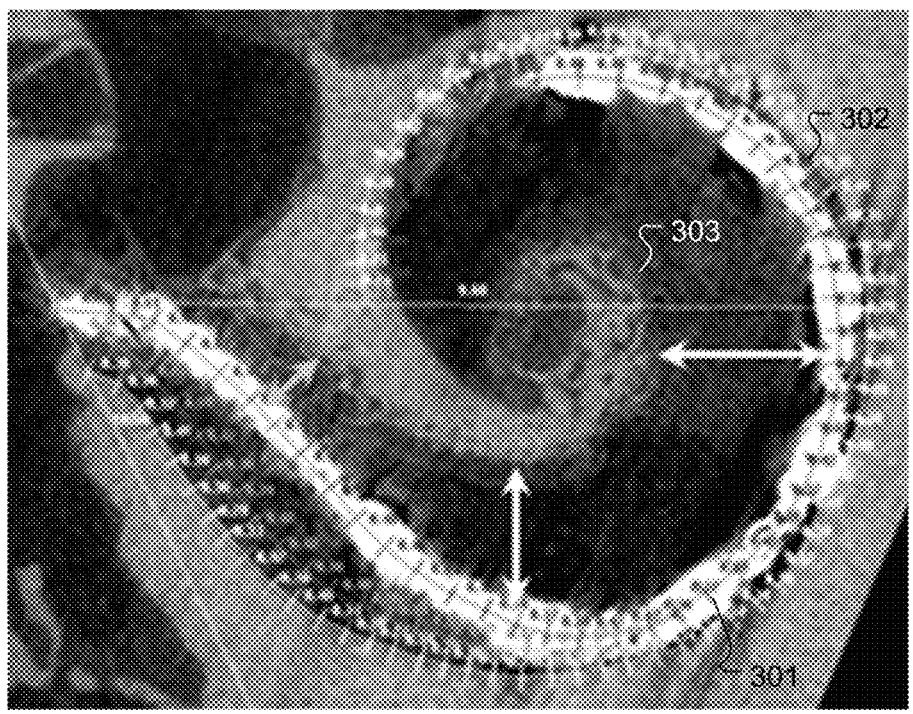
Figure 4A:
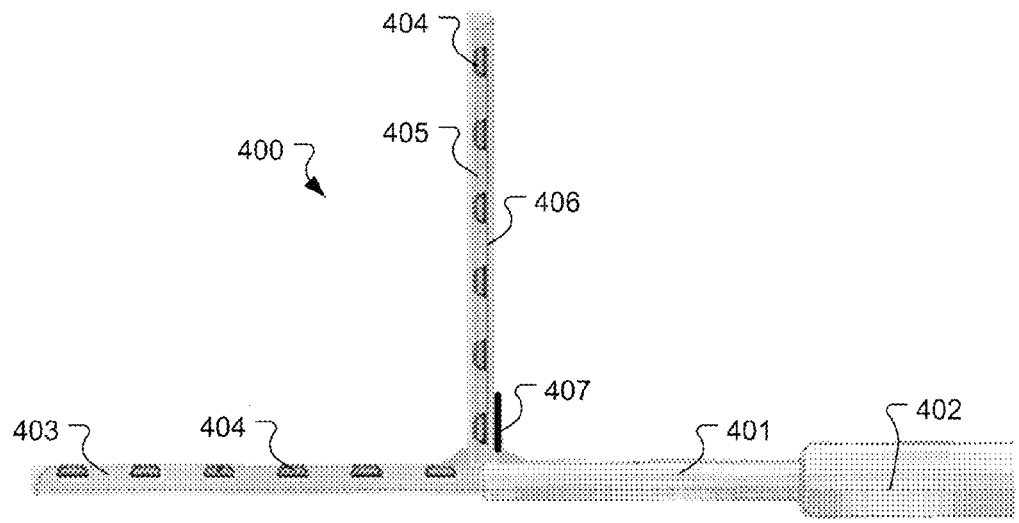
FIGS. 4A-4C show structural details of an implantable electrode array according to an embodiment of the present invention.
Figure 4B:
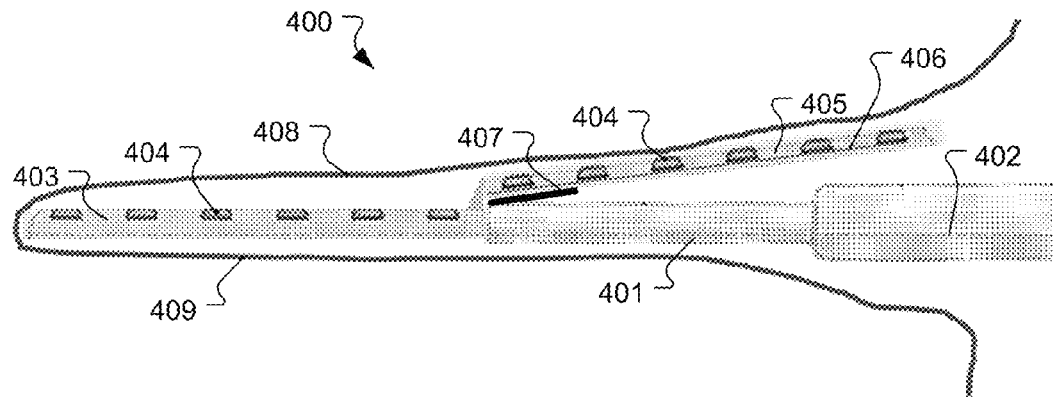
Figure 4C:
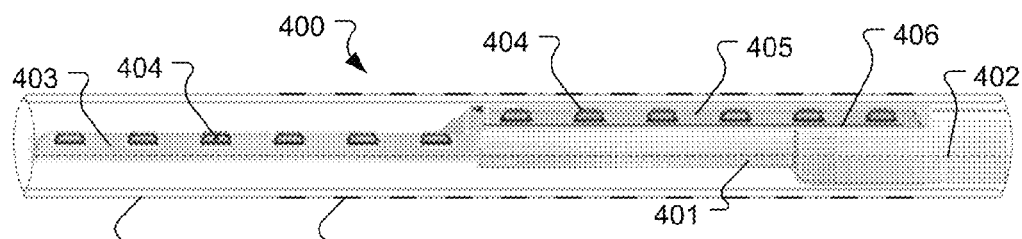

FIGS. 4A-4C show structural details of an implantable electrode array 400 that includes an array trunk 401 that extends along a center axis 402 into the scala tympani from an insertion opening in an outer surface of a patient cochlea. An apical section 403 extends out from the distal end of the array trunk 401 along the center axis 402. The apical section 403 has multiple stimulation contacts 404 distributed along its outer surface for delivering electrical stimulation signals to adjacent neural tissue. The stiffness and geometry of the apical section 403 are configured so that the apical section 403 can follow along an outer lateral wall 409 of the scala tympani during surgical insertion to attain a final insertion position towards the outer lateral wall 409 in an apical portion of the scala tympani beyond a first basal turn of the cochlea. A basal branch 405 is separate from the array trunk 401 and extends back from the distal end of the array trunk 401 towards the insertion opening. The stiffness and geometry of the basal branch 405 are configured so that when the surgical insertion is complete, the basal branch 405 attains a final insertion position towards an inner modiolar wall 408 by the first basal turn of the cochlea with the basal branch stimulation contacts 404 facing the inner modiolar wall 408. In one typical embodiment, the array trunk 401 and the basal branch 405 are stiffer and less flexible than the apical section 403 to facilitate surgical insertion.

In FIG. 4A, the basal branch 405 is shown extending away from the distal end of the array trunk 401 at a 90° angle, which is the relaxed natural position of that embodiment. In other specific embodiments, the angle between the array trunk 401 and the basal branch might be some other specific value, for example, 30°, in the relaxed natural position. During the insertion procedure, the basal branch 405 easy bends down towards the array trunk 401 for insertion into the cochlea. At the end of the insertion, the basal branch 405 is released and naturally springs back away from the array trunk 401 toward the modiolar wall 408 as shown in FIG. 4B.

In the embodiment shown in FIGS. 4A-C, the basal branch 405 has an internal support wire 406 embedded inside it, and a handling pin 407 located between the juncture of the basal branch 405 and the array trunk 401. Both the support wire 406 and the handling pin 407 promote the insertion folding of the basal branch 405, and the post-insertion springing away towards the modiolar wall 408. Because the handling pin 407 is sandwiched between the array trunk 401 and the basal branch 405, it is not a source of trauma to the nearby tissues. However, even if there is post-surgical ingrowth of tissue between the array trunk 401 and the basal branch 405, if the handling pin 407 has a sharp edge or tip, when grasped by a surgical tool it can act as retraction feature fitting and easily cut through such tissue and facilitate explantation of the electrode array 400 if needed.

In the embodiment shown in FIGS. 4A-C, there appears to be a step feature on the outer surface of the electrode array 400 in the transition zone where the apical section 403 and the basal branch 405 meet. Such a step feature may not necessarily increase the insertion trauma to the tissues it encounters. In other embodiments, the outer surface of the apical section 403 and the outer surface of the basal branch 405 may meet in a smooth continuous transition zone.

FIG. 4C shows an implantable electrode array 400 with the basal branch 405 folded against the array trunk 401 and fitted within an outer insertion tube 410 made of bio-compatible polymer material for insertion through a single cochleostomy opening in the outer surface of the patient's cochlea. The insertion tube 410 fits over the basal branch 405 and the array trunk 401 for surgical insertion into the cochlea, and then is retractable back through the insertion opening after insertion of the electrode array 400 into the cochlea to allow the basal branch 405 to open away from the array trunk 401 toward the inner modiolar wall 408. In some embodiments the insertion tube 410 may contain a longitudinal slit along its outer surface to remove it from the electrode array 400 after post-insertion retraction back outside the cochlea. The insertion tube 410 also may include one or more depth indicator marks 411 along its outer surface to help the surgeon determine when the electrode array 400 has been fully inserted. Alternatively or in addition, the array trunk 401 may include such indicator mark(s).

Figure 5:
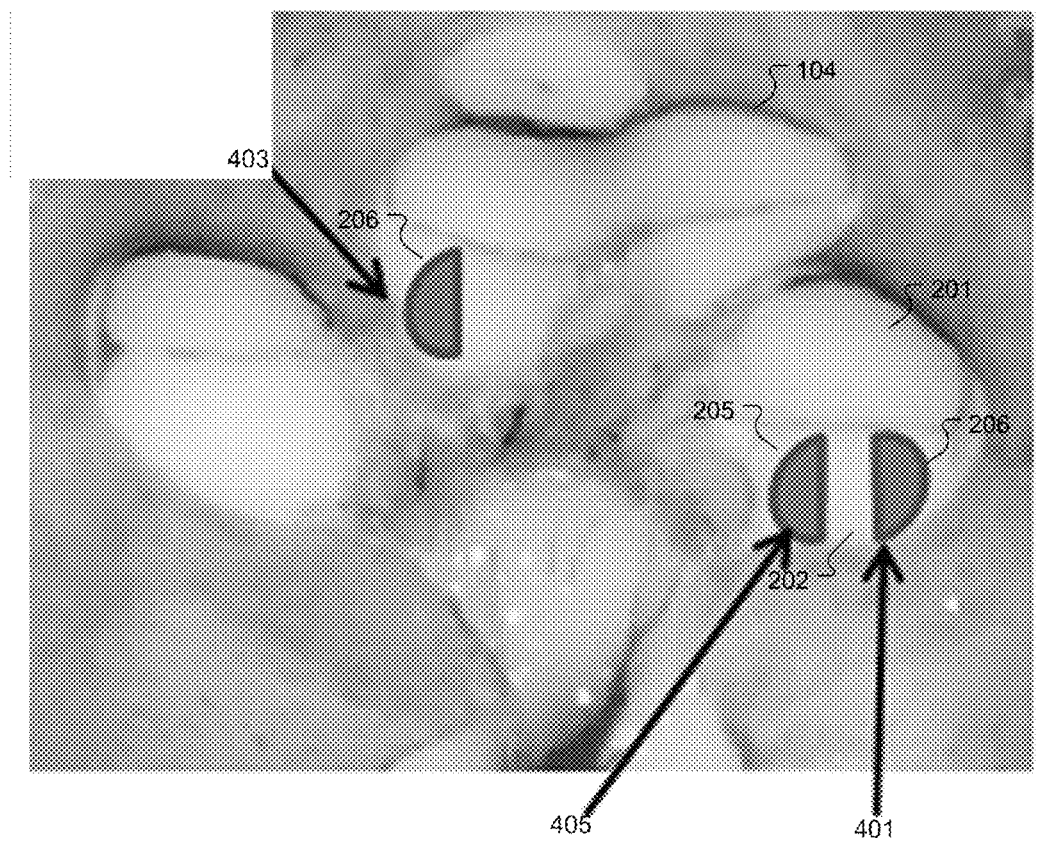
FIG. 5 is cross-sectional photograph of an implanted cochlea showing the location of the various main structural sections of the electrode array relative to the side walls.

FIG. 5 is a cross-sectional photograph of an implanted cochlea 104 showing the location of the various main structural sections of the electrode array relative to the side walls of the scala tympani 202. The apical section 403 can be seen in the upper left of the figure, against the outer lateral wall 206 in the apical portion of the cochlea 104 beyond the first basal turn. In the lower right of the figure, the array trunk 401 also is positioned against the outer lateral wall 206 in the first basal turn portion of the scala tympani 202, while the basal branch 405 is positioned against the inner modiolar wall 205. In the embodiment shown, the array trunk 401 and the basal branch 405 each have semi-circular cross-sections with adjacent flat surfaces, which helps them fit compactly together for surgical insertion. In the some embodiments, one or more of the outer surfaces of the array trunk 401, for example the inner flat surface, may incorporate a therapeutic substance (e.g., dexamethasome) that it is configured to release post-surgically to inhibit tissue ingrowth between the array trunk 401 and the basal branch 405. In even further embodiments the array trunk 401 has one or more stimulation contacts (not shown in the figures) that are distributed along its outer surface for delivering electrical stimulation signals to adjacent neural tissue.

Figure 6:
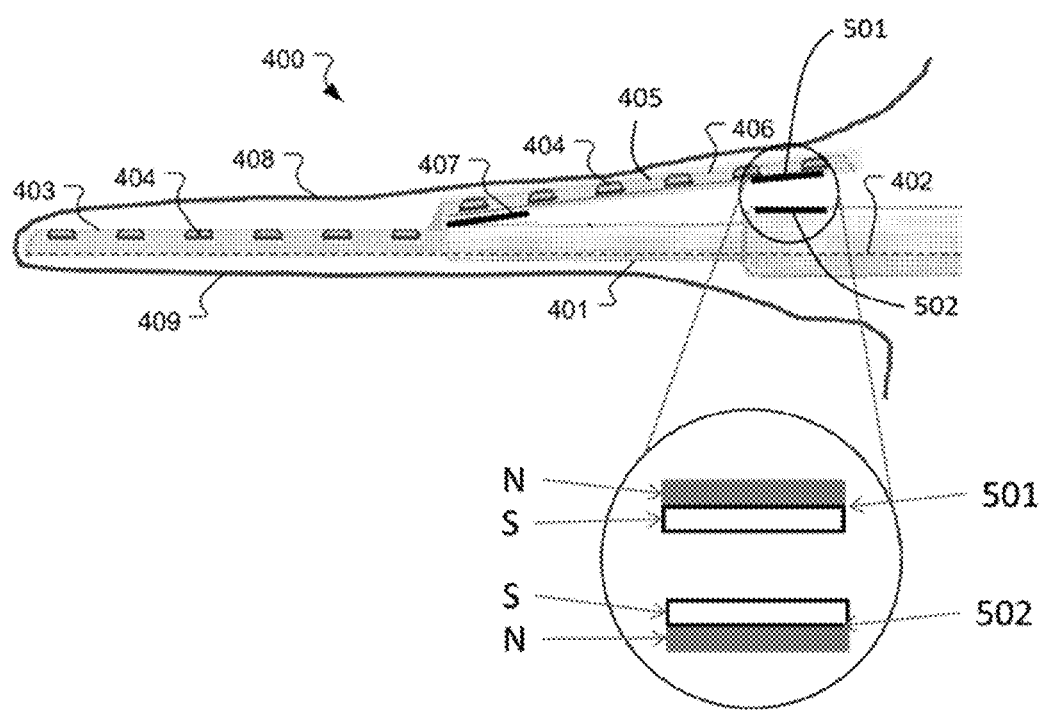
FIG. 6 shows an implantable electrode array with magnetic elements.

FIG. 6 shows an implantable electrode array 400 with magnetic elements 501 and 502 in the basal branch 405 and the array trunk 401. In FIG. 6, only one magnet element is shown in each of the basal branch 405 and the array trunk 401, but there may be more than one magnetic elements in other embodiments. In the exploded view of FIG. 6, it can be seen that the magnetic element 501 in the basal branch 405 and the magnetic element 502 in the array trunk 401 are arranged so that the same magnetic poles face each other. The resulting repelling force of the magnetic elements 501 and 502 are, therefore, promote placement of the basal branch 405 towards the modiolar wall 408.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable electrode array for a cochlear implant patient, the electrode array comprising:

an array trunk configured to extend along a center axis from an insertion opening in an outer surface of a patient cochlea into a scala tympani of the patient cochlea:

an apical section configured to extend along the center axis from a distal end of the array trunk and having an outer surface along which are distributed a plurality of stimulation contacts for delivering electrical stimulation tissues to adjacent neural tissue, wherein the apical section has stiffness and geometry characteristics configured for the apical section to follow along an outer lateral wall of the scala tympani during surgical insertion to attain a final insertion position towards the outer lateral wall in an apical portion of the scala tympani beyond a first basal turn of the cochlea; and a basal modiolar branch separate from the array trunk and extending back from the distal end of the array trunk with a non-penetrating apical end located towards the insertion opening and having an outer surface along which are distributed a plurality of stimulation contacts for delivering electrical stimulation tissues to adjacent neural tissue, wherein the basal branch has stiffness and geometry characteristics configured for non-penetrating movement of the basal branch towards an inner modiolar wall in a basal portion of the scala tympani comprising a first basal turn of the cochlea, with the basal branch stimulation contacts facing the inner modiolar wall.

2. The implantable electrode array according to claim 1, wherein the outer surface of the apical section and the outer surface of the basal branch meet in a smooth continuous transition zone.

3. The implantable electrode array according to claim 1, wherein the array trunk and the basal branch each have semi-circular cross-sections with adjacent flat surfaces.

4. The implantable electrode array according to claim 1, wherein the array trunk has an outer surface configured to post-surgically release a therapeutic substance to inhibit tissue ingrowth between the array trunk and the basal branch.

5. The implantable electrode array according to claim 1, further comprising:
 a retraction feature fitting between the array trunk and the basal branch configured to facilitate extraction of the electrode array from the scala tympani.

6. The implantable electrode array according to claim 1, further comprising:
 an outer insertion tube configured to fit over the basal branch and the array trunk for insertion into the cochlea, and retractable back through the insertion opening after insertion of the electrode array into the cochlea to allow the basal branch to open away from the array trunk toward the inner modiolar wall.

7. The implantable electrode array according to claim 6, wherein the insertion tube contains a longitudinal slit along its outer surface for removal of the insertion tube from the electrode lead after retraction.

8. The implantable electrode array according to claim 6, wherein the insertion tube includes one or more depth indicator marks along its outer surface.

9. The implantable electrode array according to claim 1, further comprising:
 an internal support wire within the basal branch that biases the basal array branch away from the array trunk toward the inner modiolar wall.

10. The implantable electrode array according to claim 1, further comprising:
 an array trunk magnetic element located on the outer surface of the array trunk facing the basal branch; and
 a basal branch magnetic element located on the outer surface of the basal branch opposite and facing the array trunk magnetic element;
 wherein the magnetic elements are arranged with like magnetic polarities facing each other to promote placement of the basal branch towards the modiolar wall.

11. A cochlear implant system having an implantable electrode array according to any one of claims 1-10.

\* \* \* \* \*